Figure 1:
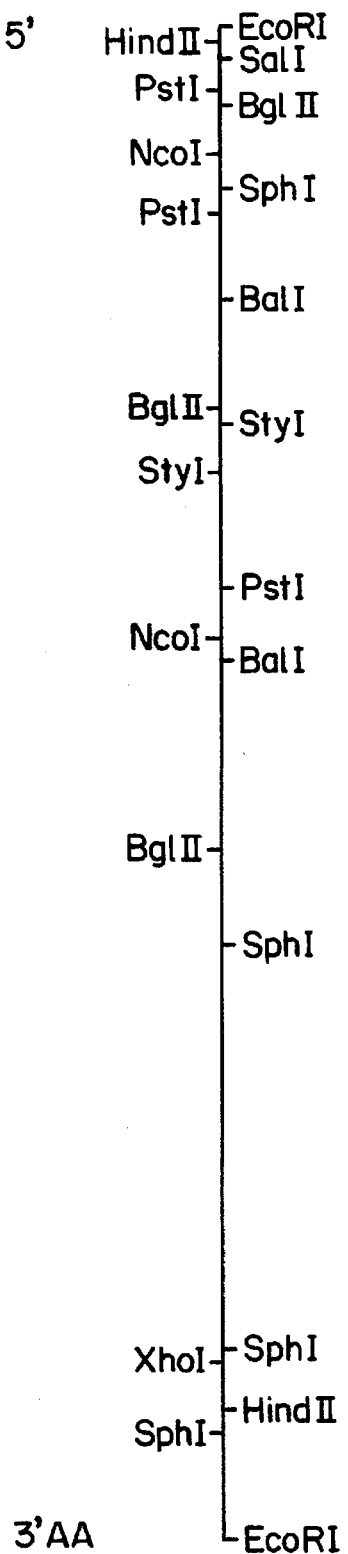

United States Patent [19]

Vermeulen et al.

[11] Patent Number: 5,637,487
[45] Date of Patent: Jun. 10, 1997

[54] *EIMERIA TENELLA* VACCINE

[75] Inventors: Arno Vermeulen, Cuyk; Rein Dijkema, Oss; Jacobus J. Kok, Nijmegen; Paul Van Den Boogaart, Oss, all of Netherlands

[73] Assignee: Akzo Nobel N.V., Arnhem, Netherlands

[21] Appl. No.: 454,218

[22] Filed: Dec. 21, 1989

[30] Foreign Application Priority Data

Jun. 21, 1989 [ZA] South Africa .......................... 89/4726

[51] Int. Cl.$^6$ .................................................. C12N 15/00
[52] U.S. Cl. ................ 435/172.3; 435/69.1; 435/235.1; 435/252.3; 935/19; 935/27; 935/31
[58] Field of Search .................... 425/69.1, 91, 172.3, 425/235, 252.3, 252.33, 320.1; 536/27; 530/350; 935/19, 27, 31, 41, 56, 58, 63, 72, 81

[56] References Cited

U.S. PATENT DOCUMENTS 4,874,705  10/1989  Andrews ........................ 435/252.33
4,973,551  11/1990  Condra ............................ 435/69.7
5,122,471   6/1992  Jenkins et al. .................... 435/252.3

OTHER PUBLICATIONS

Jenkins et al Exp Parasitol vol. 66, pp. 96–107 (1988).

Clarke et al Mol Biochem Parasitol vol. 22 pp. 79–87 (1987).

*Primary Examiner*—Douglas W. Robinson
*Assistant Examiner*—Ginny Allen Portner
*Attorney, Agent, or Firm*—Mary E. Gormley; William M. Blackstone

[57] ABSTRACT

The invention is concerned with a polypeptide of *Eimeria tenella* which can be used for the immunization of chickens against coccidiosis.

The invention also relates to a nucleic acid sequence encoding such a polypeptide. Said nucleic acid sequence is especially useful for the preparation of vector vaccines.

7 Claims, 4 Drawing Sheets

```
                                                32                                                    62
CGGAG ATG TCT GAA GTC AAC CCG GAA ATG AGC TCC TAC GAC GTC GTC CTG GTT GTT GGA GCC
      Glu Met Ser Glu Val Asn Pro Glu Met Ser Ser Tyr Asp Val Val Leu Val Val Gly Ala 92                                               122
AAC GAC ACC GTC AAT CCT GCA GCC CTT GAG CCA GGA TCA AAG ATC TCA GGA ATG CCC GTT
Asn Asp Thr Val Asn Pro Ala Ala Leu Glu Pro Gly Ser Lys Ile Ser Gly Met Pro Val 152                                              182
ATA GAG GCC TGG AAA GCT AGA CGC GTT TTT GTG CTG AAG CGG TCC ATG GCT GCT GGA TAT
Ile Glu Ala Trp Lys Ala Arg Arg Val Phe Val Leu Lys Arg Ser Met Ala Ala Gly Tyr 212                                              242
GCC AGC ATT GAA AAT CCA CTT TTC CAT CTG GAG AAC ACA CGC ATG CTC TTC GGA AAC GCA
Ala Ser Ile Glu Asn Pro Leu Phe His Leu Glu Asn Thr Arg Met Leu Phe Gly Asn Ala 272                                              302
AAG AAC ACC ACT TCT GCA GTC TTC GCC CGT GTC AAT GCC AGA GCC GAG CAA ATG CCA CCA
Lys Asn Thr Thr Ser Ala Val Phe Ala Arg Val Asn Ala Arg Ala Glu Gln Met Pro Pro 332                                              362
TCT GCT GCC CGT GAT GAC CTC GAA GCT GGA CTA CTT GAG TTC GAT AGG GAA GAA CGT GTT
Ser Ala Ala Arg Asp Asp Leu Glu Ala Gly Leu Leu Glu Phe Asp Arg Glu Glu Arg Val 392                                              422
GAT CCC TCT TCT TGG CCA TAT CCC AGG ATG GCT GTT GGT GTT CTG AGA GAC TCC AAT GGC
Asp Pro Ser Ser Trp Pro Tyr Pro Arg Met Ala Val Gly Val Leu Arg Asp Ser Asn Gly 452                                              482
TCT GTT ATG GTG CCA GTA GGT CCG AAG TTT GTG CCC AAG CTG AGG AAG TTG GCA TTC CGT
Ser Val Met Val Pro Val Ala Pro Lys Phe Val Pro Lys Leu Arg Lys Leu Ala Phe Arg 512                                              542
GTC AAT GTC GAG TCT GGT GCT GGC GCC GAT GCC GGC TTT ACT GAC GAA GAG TAC AGG AGG
Val Asn Val Glu Ser Gly Ala Gly Ala Asp Ala Gly Phe Thr Asp Glu Glu Tyr Arg Arg 572                                              602
GCT GGA GCA GAA GTC CTG TCG GGC CCC GAT GCA GTC ATT AAC CAG TCT CAA GTC CTG CTC
Ala Gly Ala Glu Val Leu Ser Gly Pro Asp Ala Val Ile Asn Gln Ser Gln Val Leu Leu 632                                              662
CGC GTT TCA GCG CCG TCG CCA GAT CTG GTT TCG CGC ATT CCT AGG GAC AAG GTC CTT ATC
Arg Val Ser Ala Pro Ser Pro Asp Leu Val Ser Arg Ile Pro Arg Asp Lys Val Leu Ile 692                                              722
AGT TAC CTA TTC CCC AGC ATC AAC CAA CAA GCT CTT GAC ATG CTA GCA CGC CAA GGC GTC
Ser Tyr Leu Phe Pro Ser Ile Asn Gln Gln Ala Leu Asp Met Leu Ala Arg Gln Gly Val 752                                              782
ACC GCA CTT GCT GTG GAT GAG GTT CCT CGC GTC ACA AGA GCA CAG AAG CTA GAC GTG AAG
Thr Ala Leu Ala Val Asp Glu Val Pro Arg Val Thr Arg Ala Gln Lys Leu Asp Val Lys 812                                              842
TCT GCT ATG CAA GGT CTC CAG GGA TAC CGC GCC GTT ATC GAA GCG TTC AAC GCT CTT CCG
Ser Ala Met Gln Gly Leu Gln Gly Tyr Arg Ala Val Ile Glu Ala Phe Asn Ala Leu Pro
```

FIG. 2A

```
                                        872                                             902
AAG CTC AGC AAA GCA TCT ATC AGT GCT GCA GGC CGT GTA GAA GCC GCT AAA GTT TTC GTC
Lys Leu Ser Lys Ala Ser Ile Ser Ala Ala Gly Arg Val Glu Ala Ala Lys Val Phe Val
                                        932                                             962
ATC GGT GCC GGT GTT GCT GGA CTA CAG GCA ATT TCT ACC GCC CAT GGT TTG GGT GCA CAA
Ile Gly Ala Gly Val Ala Gly Leu Gln Ala Ile Ser Thr Ala His Gly Leu Gly Ala Gln
                                        992                                            1022
GTA TTT GGC CAC GAT GTG CGC TCT GCA ACT CGT GAG GAA GTC GAA TCT TGC GGT GGA AAG
Val Phe Gly His Asp Val Arg Ser Ala Thr Arg Glu Glu Val Glu Ser Cys Gly Gly Lys
                                       1052                                            1082
TTC ATT GGT TTG AGA ATG GGA GAG GAG GGT GAA GTC CTC GGA GGA TAT GCA CGC GAG ATG
Phe Ile Gly Leu Arg Met Gly Glu Glu Gly Glu Val Leu Gly Gly Tyr Ala Arg Glu Met
                                       1112                                            1142
GGT GAT GCA TAT CAG AGA GGC CAA CGC GAG ATG ATT GCC AAC ACA ATC AAG CAC TGC GAT
Gly Asp Ala Tyr Gln Arg Gly Gln Arg Glu Met Ile Ala Asn Thr Ile Lys His Cys Asp
                                       1172                                            1202
GTC GTC ATC TGT ACC GCT GCT ATT CAC GGC AGA CCT TCA CCA AAG CTC ATA TCA CGC GAC
Val Val Ile Cys Thr Ala Ala Ile His Gly Arg Pro Ser Pro Lys Leu Ile Ser Arg Asp
                                       1232                                            1262
ATG TTG CGT TCA ATG AAG CCT GGC TCC GTC GTC GTA GAT CTT GCA ACA GAG TTC GGT GAT
Met Leu Arg Ser Met Lys Pro Gly Ser Val Val Val Asp Leu Ala Thr Glu Phe Gly Asp
                                       1292                                            1322
GTG CGC TCC GGC TGG GGT GGA AAC GTC GAG GTT TCG CCT AAG GAC GAC CAG ATT GTC GTT
Val Arg Ser Gly Trp Gly Gly Asn Val Glu Val Ser Pro Lys Asp Asp Gln Ile Val Val
                                       1352                                            1382
GAT GGC GTC ACT GTC ATT GGT CGC AGA CGC ATT GAG ACT CGC ATG CCC ATT CAG GCG TCT
Asp Gly Val Thr Val Ile Gly Arg Arg Arg Ile Glu Thr Arg Met Pro Ile Gln Ala Ser
                                       1412                                            1442
GAG CTG TTC TCC ATG AAC ATA TGC AAC CTC CTT GAG GAT CTT GGT GGT GGC AGC AAC TTC
Glu Leu Phe Ser Met Asn Ile Cys Asn Leu Leu Glu Asp Leu Gly Gly Gly Ser Asn Phe
                                       1472                                            1502
CGC ATC AAC ATG GAC GAC GAA GTC ATC AGA GGA TTG GTC GCA GTC TAC CAA GGT CGC AAC
Arg Ile Asn Met Asp Asp Glu Val Ile Arg Gly Leu Val Ala Val Tyr Gln Gly Arg Asn
                                       1532                                            1562
GTG TGG CAG CCA TCG CAG CCC ACT CCT GTT TCC AGG ACA CCT CCG CGC GGC CAG ATG CCG
Val Trp Gln Pro Ser Gln Pro Thr Pro Val Ser Arg Thr Pro Pro Arg Gly Gln Met Pro
                                       1592                                            1622
CCC CCG TCT GCA CCT GGT GCA CCA GCT CCT GAG AAG CCT GGT GCC TTT GCT CAA GCA CTT
Pro Pro Ser Ala Pro Gly Ala Pro Ala Pro Glu Lys Pro Gly Ala Phe Ala Gln Ala Leu
                                       1652                                            1682
GCT TCG GAT GCA TTC TTC GCA ATG TGT CTT GTT GTT GCT GCC GCT GTT GTC GGG CTC CTT
Ala Ser Asp Ala Phe Phe Ala Met Cys Leu Val Val Ala Ala Ala Val Val Gly Leu Leu
```

FIG. 2B

```
                                           1712                                                                  1742
GGC ATT GTC CTT GAC CCT GTG GAG CTC AAG CAT TTG ACT CTC CTC GGC TTG TCT CTC ATC
Gly Ile Val Leu Asp Pro Val Glu Leu Lys His Leu Thr Leu Leu Gly Leu Ser Leu Ile
                                           1772                                                                  1802
GTC GGC TAC TAC TGC GTG TGG GCC GTT ACG CCT TCG CTT CAC ACA CCA TTG ATG TCT GTG
Val Gly Tyr Tyr Cys Val Trp Ala Val Thr Pro Ser Leu His Thr Pro Leu Met Ser Val
                                           1952                                                                  1982
GGT GGA TTC TTC GTA ACT CAC CGC ATG CTG AAG ATG TTT CAG ATA TAA GGG GAG AAC CCC
Gly Gly Phe Phe Val Thr His Arg Met Leu Lys Met Phe Gln Ile End
                                           2012                                                                  2042
CTT GAG TTA ATC TTA ACT CAG AAT AAC TCT TTT TCA ATT GTA TAA ACC TGT AAC TCG TTG
                                           2072
CAA AAA AAA AAA AAA AAA AAA AAA AAA AAA AAA AAA AAA AAA AAA AAA A
```

FIG. 2C

EIMERIA TENELLA VACCINE

The invention relates to a nucleic acid sequence encoding an *Eimeria tenella* polypeptide, a recombinant nucleic acid molecule comprising such a nucleic acid sequence, a vector or a host cell containing said nucleic acid sequence, a polypeptide of *Eimeria tenella*, vaccines against coccidiosis which are based on these products as well as an antibody or antiserum immuno-reactive with said polypeptide.

Coccidiosis is a disease which is caused by intra-cellular parasites, protozoa, of the subphylum Apicomplexa and the genus Eimeria. These parasites multiply in cells which form part of the gastrointestinal tract and digestive organs of their hosts.

Due to the increasing intensive production, the damage which is caused by these parasites in the poultry industry has risen alarmingly in recent decades. The losses which poultry farmers in the Netherlands suffer every year run into millions of guilders; the loss in 1986 was about 13 million guilders. In the same year a loss of U.S. $ 300 million was suffered in the U.S., despite the use of coccidiostats.

The pathogens of coccidiosis in chickens can be subdivided into nine different types, i.e. *Eimeria acervulina, E. maxima, E. tenella, E. necatrix, E. brunetti, E. mitis, E. praecox, E. mivati* and *E. hagani*. However, some people doubt the existence of the last two types. All of these types have only the chicken as host and display a high degree of tissue specificity. The life cycles of the said types are, however, similar.

During the life cycle, the Eimeria parasites pass through a number of stages. The infectious stage (the sporulating oocyst) is taken in orally and passes into the stomach of the chicken, where the shell of the cyst bursts open as a result of the grinding action. The four sporocysts, which this oocyst contains, are released and pass into the duodenum, whereby they are exposed to bile and digestive enzymes. As a result, an opening is made in the sporocyst wall and the sporozoites present in the sporocyst are released. These sporozoites are mobile and search for suitable host cells, for example epithelium cells, in order to penetrate and to reproduce. Depending on the type, this first reproduction phase lasts 20 to 48 hours and several tens to hundreds of merozoites are formed, which each again penetrate a new host cell and reproduce. After two to sometimes five of these asexual reproduction cycles, the intracellular merozoites grow into sexual forms, the male and female gametocytes. After fertilization of the female by a male gamete, a zygote is formed which creates a cyst wall around itself. This oocyst leaves the host cell and is driven out with the faeces. If the temperature and humidity outside the chicken are relatively high and, at the same time, there is sufficient oxygen in the air, the oocyst can sporulate to the infectious stage.

Thus, no intermediate host is needed for transfer of the parasite from chicken to chicken. It is therefore conceivable that with a high degree of occupation of the available surface area the infection pressure in a chicken farm rapidly increases.

The parasite can be combatted in various ways.

In addition to using good management, coccidiosis can be combatted by using combatting agents which frequently are mixed in the feed or drinking water. However, these agents have suffered a drop in effectiveness in recent years, partly because of the high genetic capacity of the parasite to develop a resistance towards various combatting agents. In addition, a number of these agents leave residues in the meat which can give rise to problems on consumption.

Immunological prophylaxis would, therefore, constitute a much better combatting method. It is known that chickens which have lived through a sufficiently high infection are able to resist a subsequent contact with the same type of Eimeria. Resistance towards Eimeria can also be induced by infecting the birds several times with low doses of oocysts or with oocysts of weakened (non-pathogenic) strains. However, controlled administration to, specifically, large numbers of chickens for slaughter is a virtually insurmountable problem in this case. Inactivated vaccines therefore appear to be the only remaining solution.

An inactivated vaccine can consist of an antigen originating from the parasite, possibly with an adjuvant.

As an alternative for an antigen isolated from parasites, it is possible to use a product prepared with the aid of recombinant DNA technology, a technique which can be carried out according to known methods.

Moreover, vaccination can be carried out by administering a live host organism such as a bacterium, a fungus or a virus in which a gene coding the antigen has been incorporated. This organism then ensures adequate long-term synthesis of antigen so that the immune system of the chicken is adequately stimulated.

At the same time it is possible synthetically to reproduce the antigen or parts thereof and to administer this to the birds in an immunologically recognizable and stimulating form, for example bonded to a carrier protein in the presence of an adjuvant.

According to the present invention a nucleic acid sequence substantially encoding at least a part of a protein of *Eimeria tenella*, a portion of said protein being defined by the amino acid sequence represented in FIG. 2, can be applied for the preparation of a vaccine for the immunization of poultry against coccidiosis.

"Nucleic acid sequence" as used herein refers to a polymeric form of nucleotides of any length, both to ribonucleic acid sequences and to deoxyribonucleic acid sequences. In principle, this term refers to the primary structure of the molecule. Thus, this term includes double- and single stranded DNA, as well as double- and single stranded RNA and modifications thereof.

A nucleic acid sequence encoding a portion of an *Eimeria tenella* protein, said portion having an amino acid sequence shown in FIG. 2 (named EtlAl) is present in phage λgt10EtlAl. The abovementioned phage has been deposited together with the *Escherichia coli* strain BNN 102 with the Centraal Bureau voor Schimmelcultures, Baarn (The Netherlands) under no. CBS 286.89.

The phage λgt10EtlAl is prepared by first constructing a cDNA library from sporulated *E. tenella* oocysts. Screening of this cDNA library has been carried out with a labeled 296 bp EcoRI probe present in plasmid pEalA, with which the *Escherichia coli* strain K12JA221 has been transformed, which has been deposited with the Centraal Bureau voor Schimmelcultures, Baarn (The Netherlands) under no. CBS 143.88.

Subsequently, the *E. tenella* clone comprising a nucleic acid sequence according to the invention was plaque-purified. The DNA sequence inserted into λgt10EtlAl can be isolated from this phage clone. A restriction enzyme map of EtlAl is prepared (FIG. 1).

The nucleotide sequence which is determined for the cDNA section of abovementioned insertion is given in FIG. 2, likewise the amino acid sequence derived herefrom.

Said sequences only represent a portion of a protein of *Eimeria tenella*. With respect to the nucleotide sequence, the 5'-end of the gene encoding the *E. tenella* protein is not present, the N-terminus probably being absent from the amino acid sequence of the protein of *E. tenella*.

The present invention comprises a nucleic acid sequence encoding a polypeptide having an amino acid sequence shown in FIG. 2 or antigenic fragments thereof as well as a nucleic acid sequence encoding the whole protein of *E. tenella* a portion of which is defined by said amino acid sequence, or antigenic fragments thereof.

5' Nucleic acid sequences of the *E. tenella* protein not present in FIG. 2 can be obtained by standard molecular biology techniques, for example by isolating RNA of *E. tenella*, hybridizing said RNA with a primer derived from the 5' side of the present nucleic acid sequence and extending this primer with, e.g. reverse transcriptase. Thereafter, the newly synthesized DNA can be converted to its double-stranded form using standard molecular biology techniques cloned, in a suitable vector and sequenced subsequently.

Another possibility is screening the cDNA library mentioned above with a restriction fragment derived from the 5' side of the present nucleic acid sequence and isolating clones comprising DNA sequences which overlap with the nucleic acid sequence shown in FIG. 2 but comprise additional 5' sequences.

A deoxynucleic acid sequence encoding a portion of an *E. tenella* protein is shown in FIG. 2. This cDNA sequence is 1970 nucleotides in length (including the stop codon). A nucleic acid sequence substantially comprising said cDNA sequence or a fragment thereof as well as a nucleic acid sequence comprising beside said cDNA or fragments thereof additional nucleotides corresponding to the *E. tenella* protein, e.g. the complete gene encoding the *E. tenella* protein, form part of the present invention.

As is well known in the art, the degeneracy of the genetic code permits substitution of bases in a codon resulting in an other codon but still coding for the same amino acid, e.g. the codon for the amino acid glutamic acid is both GAT and GAA. Consequently, it is clear that for the expression of a polypeptide with the amino acid sequence shown in FIG. 2, or an antigenic fragment thereof use can be made of a nucleic acid sequence with such an alternative codon composition different from the nucleic acid sequence shown in FIG. 2.

Also included within the scope of the invention is a nucleic acid sequence which for at least a part displays a substantial homology with a nucleic acid sequence shown in FIG. 2, or with a fragment thereof but may comprise nucleotide substitutions, mutations, insertions, deletions, inversions etc. and encodes a protein or polypeptide which is functionally equivalent to the polypeptide shown in FIG. 2 or a fragment thereof.

The present invention comprises also a polypeptide which is encoded by a nucleic acid sequence mentioned above and which can be used for the immunization of poultry against coccidiosis.

Furthermore, a polypeptide substantially comprising at least part of the amino acid sequence represented in FIG. 2 is included in the present invention.

The term polypeptide refers to a molecular chain of amino acids and does not refer to a specific length of the product; thus, inter alia peptides oligopeptides and proteins are included within the definition of polypeptide.

It will be understood that for the particular polypeptide shown in FIG. 2, embraced herein, natural variations can exist. These variations may be demonstrated by (an) amino acid difference(s) in the overall sequence or by deletions, substitutions, insertions, inversions or additions of (an) amino acid(s) in said polypeptide.

Moreover, the potential exists in the use of recombinant DNA technology for the preparation of various derivatives of the polypeptide shown in FIG. 2, variously modified by resultant single or multiple amino acid substitutions, deletions, additions or replacements. All abovementioned modifications resulting in derivatives of the polypeptide shown in FIG. 2 or fragments thereof as well as a polypeptide comprising such a derivative or fragment thereof are included within the scope of this invention so long as the essential, characteristic activity of the polypeptide shown in FIG. 2 or an antigenic fragment thereof, remains unaffected in essence.

In addition, fragments of these polypeptides, which can be used for immunization of poultry against coccidiosis, also form part of the invention. Various methods are known for detecting such usable polypeptide fragments (termed epitopes) within a known or unknown amino acid sequence. On the basis of a known amino acid sequence, these epitopes can, for example, be determined experimentally with the aid of the screening techniques described in patent publications WO 84/03564 and WO 86/06487.

In addition, a number of regions of the polypeptide, can be designated epitopes on the basis of theoretical considerations and structural agreement with epitopes which are now known. The determination of these regions was based on a combination of the hydrophilicity criteria according to J. P. Hopp and K. R. Woods (ref. 5) and the secondary structure aspects according to P. Y. Chou and G. D. Fasman (ref. 6).

T-cell epitopes which may be necessary can likewise be derived on theoretical grounds with the aid of Berzofsky's amphiphilicity criterion (ref. 7).

For immunization against coccidiosis infection in accordance with the present invention it is also possible to use, for example, anti-idiotype antibodies or antigen-binding fragments thereof. Such antibodies are directed against the idiotype of antibodies, which, in turn, are directed against the polypeptide according to the invention. The immunogenic equivalents of the polypeptide according to the invention which have been indicated above are understood to mean, inter alia, anti-idiotype antibodies of this type.

A nucleic acid sequence according to the present invention can be ligated to various expression effecting DNA sequences, optionally containing portions of polypeptide encoding sequences such as β-galactosidase, resulting in a so called recombinant nucleic acid molecule which can be used for the transformation of a suitable host. Such hybrid DNA molecules, are preferably derived from, for example plasmids, or from nucleic acid sequences present in bacteriophages or viruses. "Transformation", as used herein, refers to the introduction of a heterologous nucleic acid sequence into a host cell, irrespective of the method used, for example direct uptake or transduction. The heterologous nucleic acid sequence may be maintained through autonomous replication or alternatively, may be integrated into the host genome. The recombinant DNA molecules preferably are provided with appropriate control sequences compatible with the designated host which can regulate the expression of the inserted nucleic acid sequence.

A suitable host cell is a cell which can be transformed by a nucleic acid sequence encoding a polypeptide or by a recombinant nucleic acid molecule comprising such a nucleic acid sequence and which can be used to express said polypeptide coded by said nucleic acid sequence. The host cell can be of procaryotic origin, e.g. bacteria such as *E. coli*, *B. subtilis* and Pseudomonas species; or of eucaryotic origin such as yeasts, e.g. *Saccharomyces cerevisiae* or higher eucaryotic cells such as insect, plant or mammalian cells, including HeLa cells and Chinese hamster ovary (CHO) cells.

The intended immunization can, for example, be effected by administering the present polypeptide, or an immunogenic section or equivalent thereof, as such to the birds, or by administering to the birds to be immunized a microorganism which has been genetically modified by a recombinant DNA and which is able to produce the polypeptide, or an immunogenic section or equivalent thereof, in situ.

For immunization of poultry against coccidiosis in accordance with the present invention, it is possible, on the one hand, to administer the present polypeptides, fragments or immunogenic equivalents as such to the birds or, on the other hand, if desired to administer microorganisms which by genetic manipulation have acquired the ability to produce the present polypeptides etc. "Subunit vaccines" is a frequently used term for the first case and the term "vector vaccines" is usually used for the second case—we will also adopt this nomenclature here.

The subunit vaccines according to the invention in general contain the polypeptides in purified form, optionally in the presence of a pharmaceutically acceptable excipient. The polypeptide can optionally be covalently bonded to a non-related protein, which, for example, can be of advantage in the purification of the fusion product. Examples are β-galactosidase, protein A, prochymosine, blood clotting factor Xa, etc.

The polypeptides for such applications can be prepared with the aid of known methods, such as by isolation from E.tenella, by means of recombinant DNA techniques or by peptide synthesis.

If desired, the polypeptides can also be modified in vivo or in vitro by, for example, glycosylation, amidation, carboxylation or phosphorylation.

In vector vaccines, the polypeptide product according to the invention is made up by a genetically manipulated organism which is itself administered to the individual to be immunized and which maintains itself for some time, or even reproduces, in the body. Diverse organisms can be used as the host for this purpose, such as, for example, bacteria such as Escherichia coli, Bacillus, or Salmonella, or viruses such as cowpox or avian pox virus. With host organisms of this type, the polypeptide can express itself as a surface antigen. In this context fusion of the said polypeptide with OMP proteins or pilus proteins of Escherichia coli or synthetic provision of signal and anchor sequences which are recognized by the organism are conceivable. It is also possible that the said immunogenic polypeptide, if desired as part of a larger whole, is released inside the animal to be immunized. In all of these cases it is also possible that one or more immunogenic products will find expression which generate protection against various pathogens and/or against various antigens of a given pathogen.

Regarding the substantial homology between the nucleic acid sequence according to the invention and a DNA fragment, encoding a protective polypeptide, derived from E. acervulina (Example 2) it is anticipated that said nucleic acid sequence or a corresponding polypeptide can be used to vaccinate poultry against other species of Eimeria, in particular E. acervulina.

It goes without saying that birds already infected by E. tenella can be treated with antibodies directed against said E. tenella. Antiserum or antibodies characteristic for a polypeptide according to the invention can be used for the therapeutic treatment of coccidiosis. Said antiserum or antibodies may be obtained by immunizing an animal with said polypeptide and isolating the antiserum therefrom.

Monoclonal antibodies directed against a polypeptide according to the invention can also be used for the therapy of birds infected with E. tenella. Said monoclonal antibodies can be produced by methods known in the art for this purpose, e.g. by immunizing mice with said polypeptide, immortalizing mouse spleen cells and selecting hybridomas producing useful antibodies. Immortal antibody-producing cell lines can also be created by direct transformation of B lymphocytes with oncogenic DNA, or transfection with Epstein-Barr virus.

Monoclonal antibodies, in particular, may be used to raise anti-idiotype antibodies by methods known in the art. These anti-idiotype antibodies may also be useful for prevention of coccidiosis in birds.

Abovementioned antiserum and monoclonal antibodies can also be used for the immunological diagnosis of birds infected with E. tenella.

EXAMPLE 1

Sporulation of E. tenella oocysts

A suspension of $5\times10^8$ E. tenella oocysts in 60 ml $10^{-4}$ M sodium dithionite was centrifuged, after which the pellet was washed once with 100 ml sterile water. The cells were resuspended in 500 ml 2% potassium bichromate and then incubated under the influence of strong aeration for 7 hours at 30° C. The oocysts were then collected by centrifuging and washed three times with 200 ml sterile water.

Isolation of RNA

For the isolation of RNA (ref. 1) the cell pellet was taken up into 2.8 ml of buffer containing 10 mM Tris acetate (pH 7.6), 75 mM sodium acetate, 1% SDS, 2 mM EDTA, 0.2 mg/ml proteinase K and 10 mM vanadyl ribonucleoside complexes. The oocysts were destroyed by vortexing for 60 seconds (max) in the presence of 13 g glass beads ($\phi$0.5 mm). 5 ml of phenol was added to the total extract and the mixture was vortexed for a further 60 seconds. After centrifuging, the supernatant liquor was pipetted off and again extracted with an equal volume of phenol/chloroform/isoamyl alcohol (25:24:1). RNA was precipitated after adding 2.5 volume ethanol and the resulting precipitate was dissolved in 800 μl Tris 10 mM, EDTA 0.1 mM pH 7.6 ($T_{10}E_{0.1}$), after which the product was extracted a further twice with an equal volume of phenol/chloroform/isoamyl alcohol (25:24:1) and twice with chloroform/isoamyl alcohol (24:1) and then precipitated with ethanol. PolyA$^+$-RNA was isolated by means of oligo(dT)-cellulose chromatography (ref. 2). Approximately 100 μg polyA$^+$-RNA was isolated from $5\times10^8$ oocysts.

cDNA synthesis

PolyA$^+$-RNA was converted to cDNA by means of the enzyme MMLV reverse transcriptase. For this purpose 25 μg polyA$^+$-RNA was dissolved in 90 μl of water and denatured for 5 minutes at 20° C. by adding mercury methyl hydroxide to 10 mM, after which β-mercaptoethanol was added to 45 mM and the mixture incubated for a further 3 minutes at 20° C. The enzyme reaction was carried out in 190 μl buffer containing 4 μg oligo(dT)$_{15}$, 150 U RNAsin$^{(R)}$, 20 mM Tris (pH 7.6), 30 mM KCl, 4 mM dithiothreitol (DTT), 2 mM MgCl$_2$, 1 mM of each dNTP and 3000 U MMLV reverse transcriptase. The reaction was stopped after 1 hour's incubation at 37° C. by adding 10 μl 0.5 M EDTA. After extraction with an equal volume of phenol/chloroform/isoamyl alcohol (25:24:1), the RNA/DNA hybrid was precipitated by adding ammonium acetate to 2 M and 2.5 volumes ethanol. The combined action of the enzymes DNA-polymerase I and RNase H (ref. 3) results in the synthesis of the second string. The pellet was dissolved in 960 μl of buffer containing 20 mM Tris (pH 7.6), 5 mM MgCl$_2$, 100 mM (NH$_4$)$_2$SO$_4$, 0.6 mM β-NAD, 16 U RNase H, 200 U DNA-polymerase I and 20 U DNA-ligase (E. coli). The incubation time was 1 hour at 12° C. and then 1 hour at 22° C., after which the reaction was stopped by adding an equal volume of phenol/chloroform/isoamyl alcohol (25:24:1) and precipitating with ethanol.

Before the cDNA was cloned in a vector suitable for this purpose it was first modified. cDNA (5 μg) was dissolved in 100 μl of buffer containing 30 mM sodium acetate (pH 5.6), 50 mM NaCl, 1 mM ZnSO$_4$ and 21 U Mung Bean Nuclease. After incubation for 30 minutes at 37° C. the reaction was stopped by adding EDTA to 10 mM and Tris to 25 mM. After extraction with phenol/chloroform/isoamyl alcohol (25:24:1) the mixture was desalinated over a Sephadex G50 column.

The following were added to the eluate (125 μl): Tris pH 7.6 to 50 mM, EDTA to 2.5 mM, DTT to 5 mM, S'-adenosylmethionine to 0.5 μm and 100 U EcoRI-methylase. After incubation for 30 minutes at 37° C., the reaction was stopped by heating for 15 minutes at 65° C., after which 1/10 volume of a solution containing Tris-HCl 100 mM, MgCl$_2$ 100 mM and NaCl 500 mM (pH 7.5) was added, and, at the same time, each dNTP to 1 mM and 12.5 U Klenow DNA-polymerase. The reaction was stopped by adding an equal volume of phenol/chloroform/isoamyl alcohol (25:24:1) after incubating for 60 minutes at 22° C. The supernatant liquor was precipitated after adding 350 μl H$_2$O and 50 μl 3 M sodium acetate (pH 5.6) with 500 μl isopropanol. After dissolving in 100 μl H$_2$O, the pellet was desalinated over Sephadex G50 and the eluate precipitated with ethanol.

After dissolving the pellet in 24 μl H$_2$O, ligation was carried out in 50 μl by adding 2 μg EcoRI linker, Tris-HCl (pH 8.0) to 30 mM, MgCl$_2$ to 10 mM, dithiothreitol to 10 mM, ATP to 1 mM, gelatin to 0.1 mg/ml and 10 U T$_4$DNA-ligase. The reaction was stopped after 16 hours' incubation at 4° C. by heating (for 15 minutes at 70° C.) after which cutting was carried out with restriction endonuclease EcoRI in 210 μl buffer containing 100 mM Tris-HCl (pH 7.6), 50 mM NaCl, 10 mM MgCl$_2$, 2.5 mM DTT and 500 U EcoRI. After 90 minutes' incubation at 37° C., the reaction was stopped by means of extraction with an equal volume of phenol/chloroform/isoamyl alcohol (25:24:1). The supernatant liquor was precipitated with 2.5 volume ethanol after adding sodium acetate (pH 5.6) to 300 mM cDNA and linkers were separated by means of a Biogel A15m column. The cDNA was precipitated with ethanol, after which the precipitate was dissolved in Tris-HCl 10 mM, EDTA 0.1 mM (pH 7.6). The cDNA molecules were then cloned in phage λgt10 (4).

EXAMPLE 2

Screening of the E. tenella cDNA library with E. acervulina DNA

The 296 bp EcoRI fragment from pUC18/EalA was labeled with digoxigenin-dUTP by random priming, exactly following the protocol going with the "DNA labeling and detection kit, non-radioactive" from Boehringer, Mannheim (Cat. No. 1093657).

Filters containing immobilized DNA from the E. tenella cDNA library described above were prepared as described by Maniatis et al. (2) and probed by the freshly denatured (10 min. 95° C.), labeled E. acervulina fragment for 16 hours at 42° C. according to the manufacturer's instructions. Filters were washed as follows: twice for fifteen minutes with 2 x SSC, 0.1% (w/v) SDS (1 x SSC is 0.015 mol/l sodium citrate pH 7.0 plus 0.15 mol/l NaCl) at room temperature, twice for fifteen minutes with 1 x SSC, 0.1% (w/v) SDS at 68° C., twice for thirty and once for fifteen minutes with 0.1 x SSC, 0.1% (w/v) SDS at 68° C. and twice with PBS-tween (7.65 g/l NaCl, 0.91 g/l Na$_2$HPO$_4$·2H$_2$O, 0.21 g/l KH$_2$PO$_4$, 0.05% (v/v) Tween 80, pH 7.3) for 15 minutes at room temperature.

The filters were then reacted with a 1:5000 dilution in PBS-tween of polyclonal sheep anti-digoxigenin Fab-fragments, conjugated to alkaline phosphatase, for thirty minutes at room temperature. After washing the filters for four times fifteen minutes with PBS-tween at room temperature and once for fifteen minutes with 0.01 M Tris-HCl pH 8.0, 0.15 M NaCl, binding of the alkaline phosphatase to the filters was detected upon incubation with a solution of 0.33 g/l Nitroblue tetrazolium and 0.17 g/l 5-bromo-4-chloro-3-indolyl-phosphate in 0.1 M Tris-HCl pH 9.6, 0.1 M NaCl, 0.01 M MgCl$_2$. One out of every 400 λgt10 E. tenella clones reacted with the E. acervulina probe; ten of these, called E. tenellalAl to 10 (λgt10EtlAl to 10) were plaque-purified. λgt10EtlAl together with the Escherichia coli strain BNN102 have been deposited with the Centraal Bureau voor Schimmelcultures, Baarn (The Netherlands) under no. CBS 286.89. From subclones of this cDNA insert, prepared either in plasmid pGEM4Z or bacteriophage M13 (2), the complete nucleotide sequence was determined according to the manufacturer's instructions (USB sequence kit).

References

1) J. Pasternak et al.: Mol. & Bioch. Par. 3 (1981), 133–142.
2) T. Maniatis et al.: Molecular Cloning (Cold Spring Harbor Laboratory) 1982.
3) U. Gubbler et al.: Gene 25 (1983), 263–269.
4) T. V. Huynk et al.: DNA Cloning Techniques: A Practical Approach; D. Glover Oxford (1984).
5) J. P. Hopp et al.: Proc. Natl.Acad. Sci. U.S.A. 78 (1981), 3824–3828.
6) P. Y. Chou et al.: Advances in Enzymology 47 (1987), 45–148.
7) M. F. Good et al.: Science 235 (1987), 1059–1062.

Legends to the figures

FIG. 1

Restriction enzyme map of a DNA fragment, EtlAl, inserted into phage λgt10EtlAl.

FIG. 2

Nucleotide sequence of the DNA inserted into phage λgt10EtlAl and the deduced amino acid sequence of EtlAl.

We claim:

1. An isolated and purified nucleic acid molecule that encodes a protein of Elmerie tenella, wherein the protein consists of the amino acid sequence represented in FIG. 2.

2. An isolated and purified nucleic acid molecule consisting of the deoxvribonucleic acid sequence represented in FIG. 2.

3. A recombinant nucleic acid comprising a nucleic acid molecule according to claim 1, operably linked to heterologous control sequences enabling expression of said nucleic acid molecule.

4. A viral vector comprising the recombinant nucleic acid according to claim 3.

5. A transformed host cell containing a nucleic acid molecule according to claim 1.

6. A transformed host cell containing a recombinant nucleic acid according to claim 3.

7. A transformed host cell transformed by a viral vector according to claim 4.

* * * * *

UNITED STATES PATENT AND TRADEMARK OFFICE
CERTIFICATE OF CORRECTION

PATENT NO. : 5,637,487
DATED : June 10, 1997
INVENTOR(S) : Vermulen et al.

It is certified that error appears in the above-indentified patent and that said Letters Patent is hereby corrected as shown below:

Column 8, line 43, claim 1, please delete "Elmerie" and replace with -- Eimeria --; and line 46, claim 2, please delete "deoxvribonucleic" and replace with -- deoxyribonucleic --

Signed and Sealed this

Fourteenth Day of October, 1997

Attest:

BRUCE LEHMAN

Attesting Officer

Commissioner of Patents and Trademarks